United States Patent
Govari et al.

(10) Patent No.: US 12,336,823 B2
(45) Date of Patent: Jun. 24, 2025

(54) CATHETER CONNECTION CONFIGURATION SYSTEM

(71) Applicant: Biosense Webster (Israel) Ltd., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 715 days.

(21) Appl. No.: 17/542,789

(22) Filed: Dec. 6, 2021

(65) Prior Publication Data

US 2023/0172512 A1    Jun. 8, 2023

(51) Int. Cl.
    *A61B 5/273*    (2021.01)
    *A61B 5/283*    (2021.01)
    *A61B 5/367*    (2021.01)

(52) U.S. Cl.
    CPC .............. *A61B 5/273* (2021.01); *A61B 5/283* (2021.01); *A61B 5/367* (2021.01)

(58) Field of Classification Search
    CPC ......... A61B 5/273; A61B 5/283; A61B 5/367; A61B 18/1492; A61B 2017/00053; A61B 2034/2051; A61B 2090/372; A61B 18/1206; A61B 2018/00178; A61B 2562/0223; A61B 34/25; A61B 18/00; A61B 18/12; A61B 2018/00351; A61B 2018/00577; A61B 2018/00636; A61M 25/0043; A61M 25/01
    See application file for complete search history.

(56) References Cited

U.S. PATENT DOCUMENTS

| | | | |
|---|---|---|---|
| 5,342,356 A | 8/1994 | Ellman et al. |
| 5,391,199 A | 2/1995 | Ben-Haim |
| 6,239,724 B1 | 5/2001 | Doron et al. |
| 6,332,089 B1 | 12/2001 | Acker et al. |
| 6,484,118 B1 | 11/2002 | Govari |
| 6,508,809 B1 | 1/2003 | Bacher |
| 6,618,612 B1 | 9/2003 | Acker et al. |
| 6,690,963 B2 | 2/2004 | Ben-Haim et al. |

(Continued)

FOREIGN PATENT DOCUMENTS

| | | |
|---|---|---|
| WO | 199600099 A1 | 1/1996 |
| WO | 1996005768 A1 | 2/1996 |

OTHER PUBLICATIONS

European Search Report for corresponding EPA No. 22211476.1 dated Apr. 12, 2023.

*Primary Examiner* — Ronald Hupczey, Jr.
*Assistant Examiner* — Ana Veruska Guerrero (57) ABSTRACT

In one example, a medical system includes a display, a console including a plurality of ports configured to be coupled with the catheters via respective cables, the catheters having respective first electrical channel profiles, the ports having respective second electrical channel profiles, and processing circuitry configured to receive user input selecting respective ones of the catheters to be used in a medical procedure. find a connection configuration with which to couple the respective ones of the catheters with ones of the ports, responsively to the respective first electrical channel profiles of the respective ones of the catheters and the respective second electrical channel profiles of the ports, and render the connection configuration to the display.

15 Claims, 8 Drawing Sheets

(56) References Cited

U.S. PATENT DOCUMENTS

| | | |
|---|---|---|
| 7,756,576 B2 | 7/2010 | Levin |
| 7,848,787 B2 | 12/2010 | Osadchy |
| 7,869,865 B2 | 1/2011 | Govari et al. |
| 2002/0006455 A1 | 1/2002 | Levine |
| 2003/0120150 A1 | 6/2003 | Govari |
| 2004/0068178 A1 | 4/2004 | Govari |
| 2008/0281312 A1 | 11/2008 | Werneth |
| 2011/0045680 A1 | 2/2011 | Beller et al. |
| 2011/0125149 A1* | 5/2011 | El-Galley .............. A61B 17/00 606/34 |
| 2013/0088452 A1* | 4/2013 | Glaser-Seidnitzer ....................... G06F 3/0488 345/173 |
| 2014/0171785 A1* | 6/2014 | Zino ................ A61B 17/00234 606/1 |
| 2017/0087715 A1* | 3/2017 | Komuro ............. A61B 90/361 |
| 2017/0333013 A1* | 11/2017 | Shah ..................... A61B 17/00 |
| 2018/0235509 A1 | 8/2018 | Doron |

\* cited by examiner

CATHETER CONNECTION CONFIGURATION SYSTEM

FIELD OF THE DISCLOSURE

The present disclosure relates to medical systems, and in particular, but not exclusively, to catheter devices.

BACKGROUND

A wide range of medical procedures involve placing probes, such as catheters, within a patient's body. One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Catheters are inserted into the heart chamber and optionally around the heart chamber during such procedures. In most procedures, multiple catheters are inserted into the patient. Catheters may include mapping, ablation, temperature sensing and image sensing catheters. Some catheters are dedicated for placement in specific parts of the anatomy, e.g., coronary sinus, esophagus, atrium, ventricle. The catheters have multiple electrical channels, some more than others depending on the number of sensors and electrodes included in each catheter. The number and type of catheters depends on the procedure and on the physician preferred workflow.

BRIEF DESCRIPTION OF THE DRAWINGS

The present disclosure will be understood from the following detailed description, taken in conjunction with the drawings in which.

DESCRIPTION OF EXAMPLE EMBODIMENTS

Overview

A mapping and ablation system may include a console, which allows connecting multiple catheters to the console using cables via respective ports provided in the console. Catheters may be plugged into any one of a plurality of the ports based on selecting the right cable for the selected port. The ports may differ in the number of pins that they have, e.g., a 25-pin port, a 100-pin port, corresponding to the number of electrical channels (e.g., electrogram channels and optionally ablation and/or position signal channels). By way of example, a catheter that only requires a 25-pin port might be connected to a 100-pin port and then another catheter that needs a 100-pin port cannot be connected, or cannot be easily connected, at the same time as the other catheter. The operator may be confused as to which catheter should be connected to which port and may not make the best selection. The operator may also be confused as to which cable to use for connecting to the available ports. By way of another example, a console may include 8 ports with 96 electrogram channels divided among the 8 ports. If a port with 34 electrogram channels is used for a catheter with ten electrodes or for a catheter performing ablation only, then the electrogram channels are wasted and another catheter needing 30 electrogram channels cannot then also be connected to the console and have access to the 30 electrogram channels needed for that catheter. An additional problem is that cables may be sterile and separately packaged in blister packaging. If the connection protocol is unclear, the operator may open the wrong cable package and once the blister packaging is opened, the cable is no longer sterile, thereby leading to wastage.

Examples of the present disclosure solve at least some of the above problems by providing an automated catheter connection configuration system and method. In some examples, the physician or operator may select the catheters that will be used in a medical procedure from a list of available catheters, for example, using pull down lists. Software then finds a connection configuration with which to couple the selected catheters with the ports. The connection configuration is then rendered to a display to show the physician how to couple the catheters to the ports. The connection configuration may also indicate the cables that should be used to connect the respective catheters to the ports.

In another example, the physician or operator may select a particular medical procedure that is to be performed and the software may provide a relevant list of catheters and/or probes that may be used in the procedure. In some examples, the physician may select a workflow template thereby selecting the catheters to be used in a medical procedure. For example, one or more physicians may save different workflow templates including the catheters used in the workflow and optionally associated procedure types performed by each catheter. The selected workflow template may be retrieved from memory thereby selecting the catheters (and procedure types) to be used. The catheters and optionally the procedure types to be performed in the selected workflow template are displayed. The displayed catheters and procedure types may be changed by the physician.

In some examples, the electrical channel profiles of the catheters (e.g., how many electrogram, ablation, and position channels the respective catheters have) are compared to the electrical channel profiles of the available ports. The connection configuration may be optimized by first comparing the catheter having the largest number of electrical channels to the ports, followed by the next largest, and so on. In some examples, the procedure types (e.g., mapping, imaging, and/or ablation) used by the respective catheters may also selected by the physician and used by the software to determine the connection configuration. By way of example, if a catheter has both mapping electrodes and ablation electrodes, but the catheter is only going to be used for ablation, then the catheter does not need port connections for the mapping electrodes, and vice-versa. In another example, a mapping and/or ablation catheter may have position sensing and/or temperature sensing capability. If the sensing feature is not being used for a particular workflow, then the catheter may not need port connections for the sensors, e.g., position and/or temperature sensors. By way of another example, if after performing the matching process, the software cannot find a connection configuration in which all the selected catheters can be connected to the ports at the same time, the software may then try to find a connection configuration in which the catheters used for mapping are connected for a first time period to the ports, and then the catheters used for ablation are connected for a second time period to the ports, based on the assumption that mapping is normally followed by ablation.

In some examples, the ports are statically labeled (i.e., the labels do not change over time), for example, using colors, shapes, names and/or numbers. The cable and/or cable packaging may also be labeled, for example, using colors, shapes, names and/or numbers. The connection configuration rendered to the display may list the port label and cable/cable packaging label for each of the selected catheters. For example, catheter A (e.g., a basket catheter) should be connected to port 1 using the red cable, catheter B (e.g., a balloon catheter) should be connected to port 5 using the green cable and catheter C (e.g., a focal catheter) should be connected to port 4 using the blue cable.

In some examples, the ports are dynamically labeled using ("mini") port displays adjacent to each port. The port displays may indicate the cable that should be connected to each port, while a main display indicates the cable that should be connected to each catheter. For example, the main display may indicate that catheter A should be connected using the red cable, catheter B using the green cable, and catheter C using the blue cable. Then the port displays of ports 1, 5, and 4 display "red", "green", and "blue", respectively, indicating the cables that should be connected to the ports.

In some examples, the port displays may indicate the catheter and cable that should be connected to each port. For example, the port display of port 1 may indicate that catheter A should be connected using the red cable, the port display of port 5 may indicate that catheter B should be connected using the green cable, and the port display of port 4 may indicate that catheter C should be connected using the blue cable.

System Description

Figure 1:
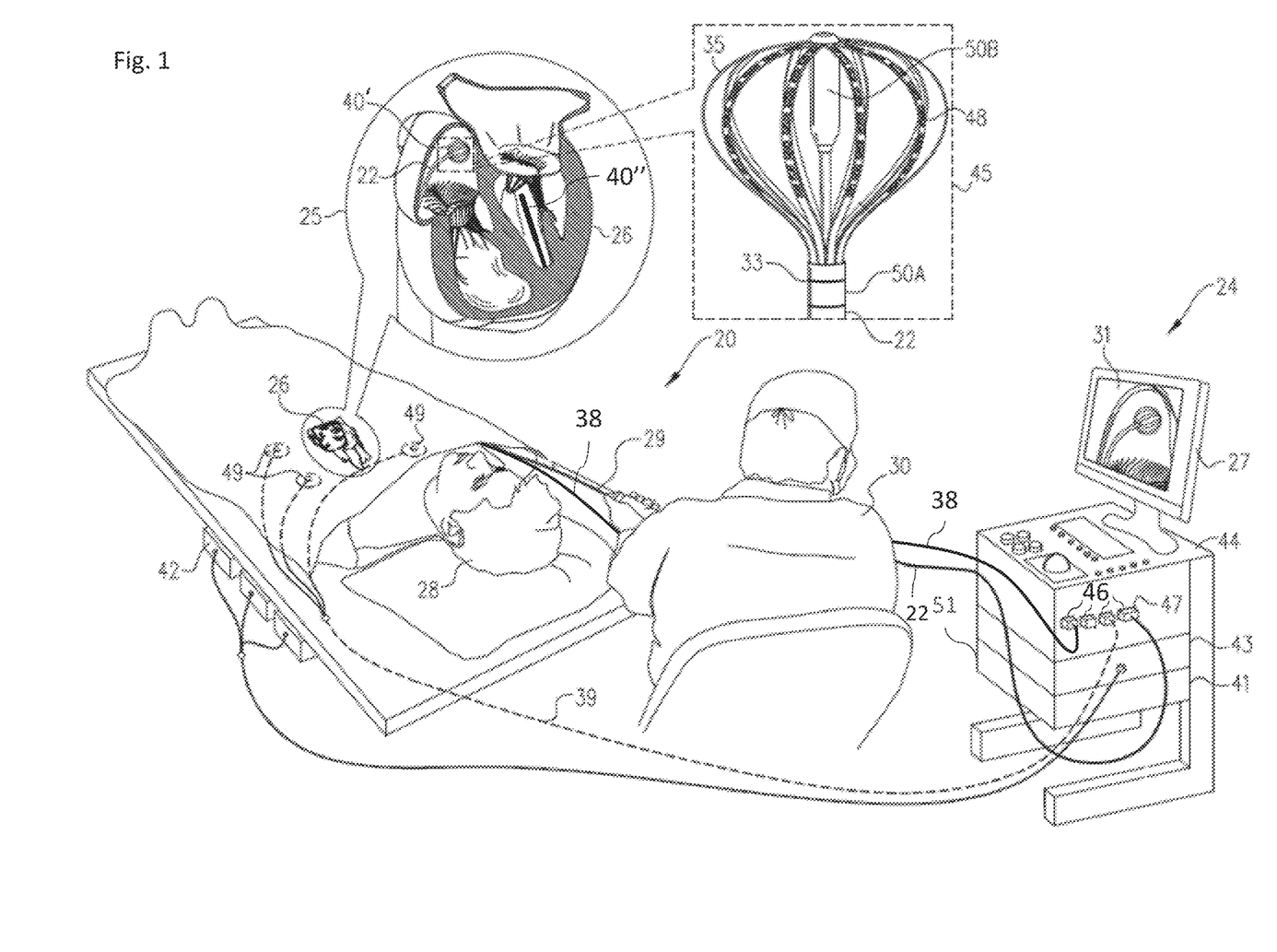
FIG. 1 is a schematic, pictorial illustration of a catheter tracking system constructed and operative in accordance with an example of the present disclosure.

Reference is now made to FIG. 1, which is a schematic, pictorial illustration of a medical system 20, in accordance with an example of the present disclosure. The system 20 includes a catheter 40' configured to be inserted into a body part (e.g., a chamber of a heart 26) of a living subject (e.g., a patient 28). A physician 30 navigates the catheter 40' (for example, a basket catheter produced by Biosense Webster, Inc. of Irvine, CA, USA), seen in detail in inset 45, to a target location in the heart 26 of the patient 28, by manipulating a deflectable segment of an insertion tube 22 of the catheter 40'. In the pictured example, physician 30 uses catheter 40' to perform electro-anatomical mapping of a cardiac chamber.

The catheter 40' includes a distal end 33. The distal end 33 of the catheter 40' includes an assembly 35 (e.g., a basket assembly as shown in FIG. 1 or a balloon assembly or any suitable distal end assembly, e.g., grid, flexible splines or a focal catheter) on which at least one (e.g., multiple) catheter electrode(s) 48 (only some labeled for the sake of simplicity) are disposed. The electrodes 48 are configured to contact tissue at respective locations with the chamber of the heart.

FIG. 1 also shows another catheter 40" inserted into a chamber of the heart 26. The catheter 40" may be any suitable catheter, for example, a pacing catheter or an imaging catheter such as an ultrasound catheter or a focal catheter. The catheter 40" is connected via a cable 38 to a port 46 on a console 24. The console 24 includes other ports 46 for connecting other catheters to the console 24.

The distal end 33 of the catheter 40' may comprise magnetic coil sensors 50A and 50B. The magnetic coil sensor 50A is shown in inset 45 at the distal edge of insertion tube 22 (i.e., at the proximal edge of basket assembly 35). Magnetic coil sensors 50A and 50B and electrodes 48 are connected by wires running through insertion tube 22 to various driver circuitries in console 24.

In some examples, system 20 comprises a magnetic-sensing sub-system. Patient 28 is placed in a magnetic field generated by a pad containing multiple magnetic field generator coils 42, which are driven by a magnetic sensing driver unit 43. The magnetic field generator coils 42 are configured to generate respective alternating magnetic fields, having respective different frequencies, into a region where a body-part (e.g., the heart 26) of a living subject (e.g., the patient 28) is located. The magnetic coil sensors 50A and 50B are configured to output electrical signals responsively to detecting the respective magnetic fields. The generated signals are transmitted to console 24 and become corresponding electrical inputs to processing circuitry 41.

In some examples, the processing circuitry 41 uses position-signals received from the electrodes 48 or body surface electrodes 49, and the magnetic sensor 50 to estimate a position of the assembly 35 inside a body part, such as inside a cardiac chamber. In some examples, the processing circuitry 41 correlates the position signals received from the electrodes 48, 49 with previously acquired magnetic location-calibrated position signals, to estimate the position of the assembly 35 inside the body part. The position coordinates of the electrodes 48 may be determined by the processing circuitry 41 based on, among other inputs, measured impedances, voltages or on proportions of currents distribution, between the electrodes 48 and the body surface electrodes 49.

The method of position sensing using current distribution measurements and/or external magnetic fields is implemented in various medical applications, for example, in the Carto® system, produced by Biosense Webster Inc. (Irvine, California), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1.

Processing circuitry 41, typically part of a general-purpose computer, is further connected via a suitable front end and interface circuits 44, to receive signals from body surface-electrodes 49. Processing circuitry 41 is connected to surface-electrodes 49 by wires running through a cable 39 to the chest of patient 28. The catheter 40' includes a connector 47 disposed at the proximal end 29 of the insertion tube 22 for coupling with the processing circuitry 41 via one of the ports 46 of the console 24. In some examples, processing circuitry 41 renders to a display 27, a representation 31 of at least a part of the catheter 40' and a body-part.

Processing circuitry 41 is typically programmed in software and/or firmware to carry out the functions described herein. The software may be downloaded to the computer in electronic form, over a network, for example, or it may, alternatively or additionally, be provided and/or stored on non-transitory tangible media, such as magnetic, optical, or electronic memory. The system 20 may also include a memory 51 used by the processing circuitry 41.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

Figure 2:
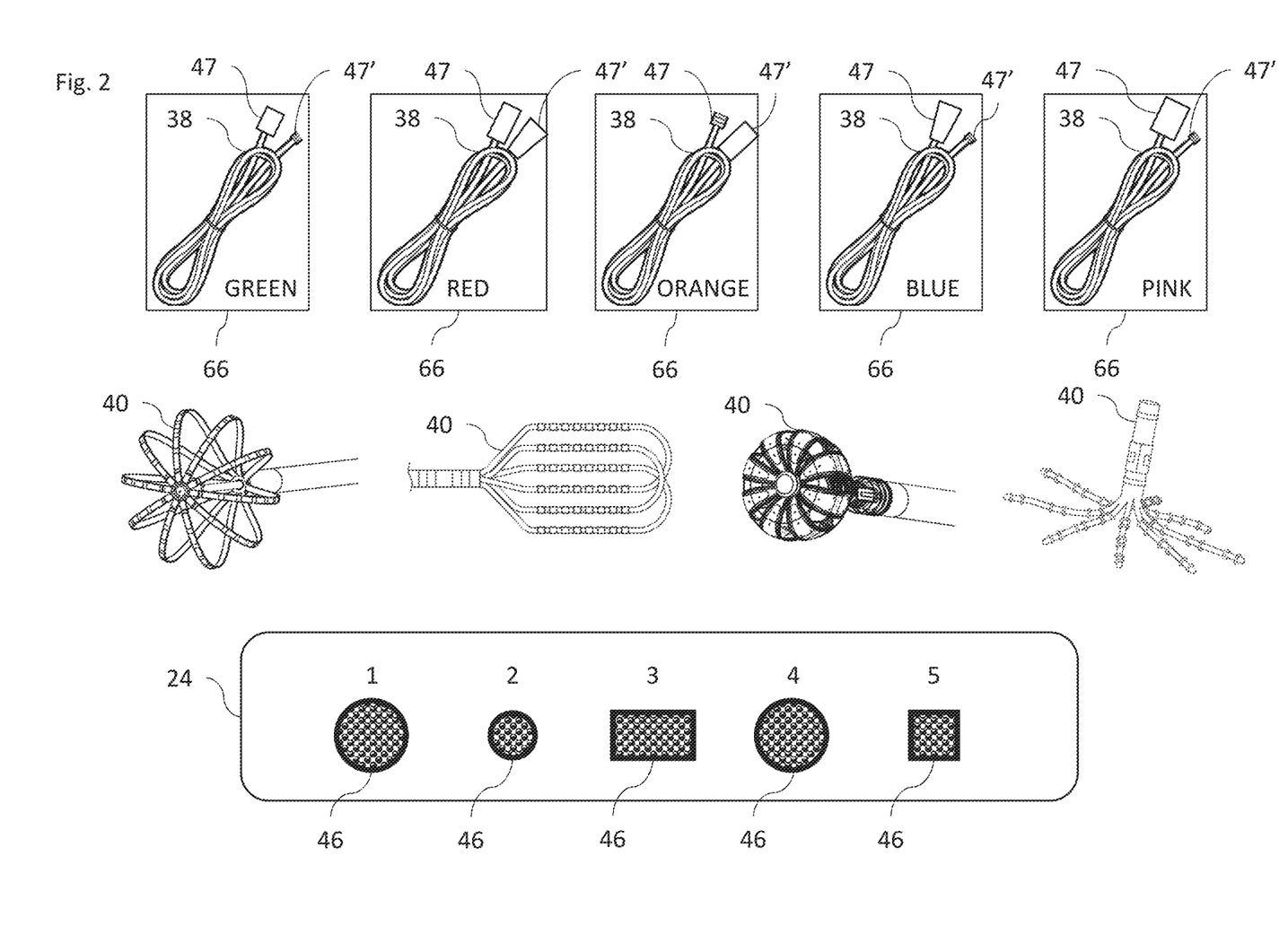
FIG. 2 is a schematic view of different cables, catheters, and console ports in the system of FIG. 1.

Reference is now made to FIG. 2, which is a schematic view of different cables 38, catheters 40 configured to be inserted into a body part of a living subject, and console ports 46 in the system 20 of FIG. 1.

The catheters 40 may include a respective electrical connector at their proximal ends with which to couple the catheters 40 via respective ones of the cables 38 with the ports 46. The catheters 40 may have respective electrical channel profiles. Some of the electrical channel profiles of the catheters 40 may be the same, and in some cases the electrical channel profiles of the catheters 40 may all be different. An electrical channel profile of a catheter defines the total number of electrical connections to/from the catheter via the catheter electrical connector and the arrangement of those electrical connections in the catheter electrical connector (e.g., an arrangement of the pins of the catheter electrical connector). The electrical channel profile of the catheter may also include the number of sub-categories of electrical channels and their arrangement among the pins. For example, the electrical channel profile of a catheter may include X electrogram electrical connections (e.g., to X corresponding mapping electrodes of the catheter), Y ablation electrical connections (e.g., to Y ablation electrodes of the catheter), and Z position signal electrical connections to carry signals to/from position signals in the catheter, and so on. The electrical channels may also include electrical connections to carry signals to imaging modalities such as ultrasound. Each of X, Y and Z represents an integer number, e.g., a number between 1-500.

The console 24 includes the ports 46 configured to be coupled with the catheters 40 via respective ones of the cables 38. The ports 46 may have respective electrical channel profiles. Some of the electrical channel profiles of the ports 46 may be the same, and in some cases the electrical channel profiles of the ports 46 may all be different. An electrical channel profile of a port defines the total number of electrical connections through the port and the arrangement of those electrical connections in the port (e.g., an arrangement of the pins of the port). The electrical channel profile of the port may also include the number of sub-categories of electrical channels and their arrangement among the pins. For example, the electrical channel profile of the port may include X electrogram electrical connections (e.g., connected to electrogram processing circuitry in the console 24), Y ablation electrical connections (e.g., connected to ablation power generator(s) in the console 24), and Z position signal electrical connections (e.g., connected to position tracking circuitry in the console 24), and so on. The electrical channels may also include electrical connections to carry signals to imaging processing circuitry in the console 24.

In some examples, the ports 46 are provided with indications which are static (i.e., the indications do not change), for example, using colors, shapes, names and/or numbers. The ports 46 shown in FIG. 2 are labeled 1-5.

Each of the cables 38 includes two respective electrical connectors 47 and 47', one connector 47 to couple with one or more of the ports 46 and another connector 47' to couple with one or more of the catheters 40. The cables 38 may have respective electrical channel profiles. An electrical channel profile of a cable defines the total number of electrical connections through the cable and the arrangement of those electrical connections in the electrical connectors of the cable (e.g., an arrangement of the pins of the electrical connectors). The electrical channel profile of the cable may also include the number of sub-categories of electrical channels and their arrangement among the pins of the respective electrical connectors. For example, the electrical channel profile of the cable may include X electrogram electrical connections (e.g., for connection to electrogram channels of the catheters 40 and ports 46), Y ablation electrical connections (e.g., for connection to ablation channels of the catheters 40 and ports 46), and Z position signal electrical connections (e.g., for connection to position signal channels of the catheters 40 and ports 46), and so on.

The cables 38 and/or cable packaging 66 may be provided with indications (e.g., labels), for example, using colors, shapes, names and/or numbers. For example, one cable 38 and/or its connectors may be green, or include a green band, and/or include a green label on the cable packaging 66.

Figure 3:
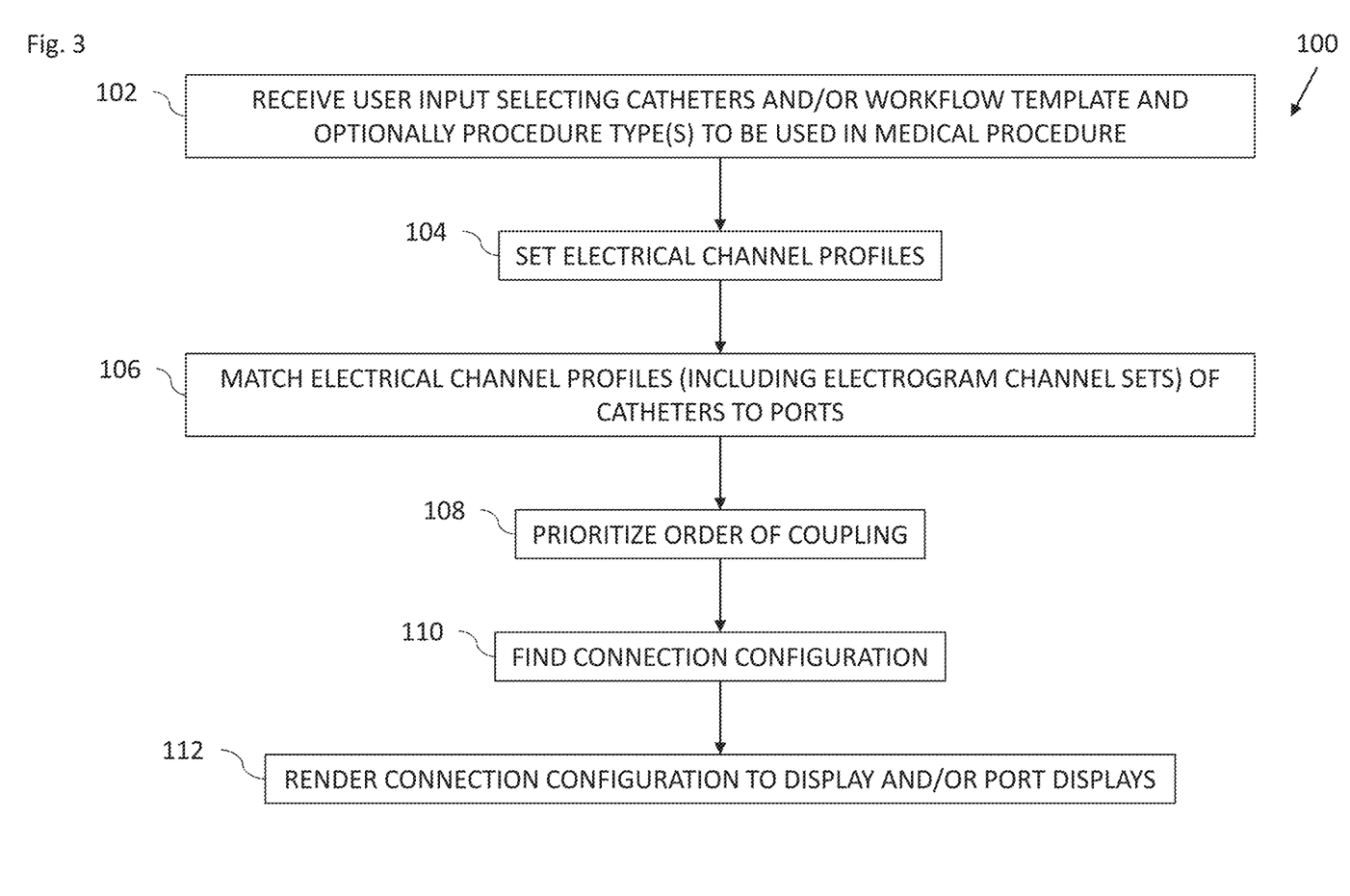
FIG. 3 is a flowchart including steps in a method of operation of the system of FIG. 1.
Figure 4:
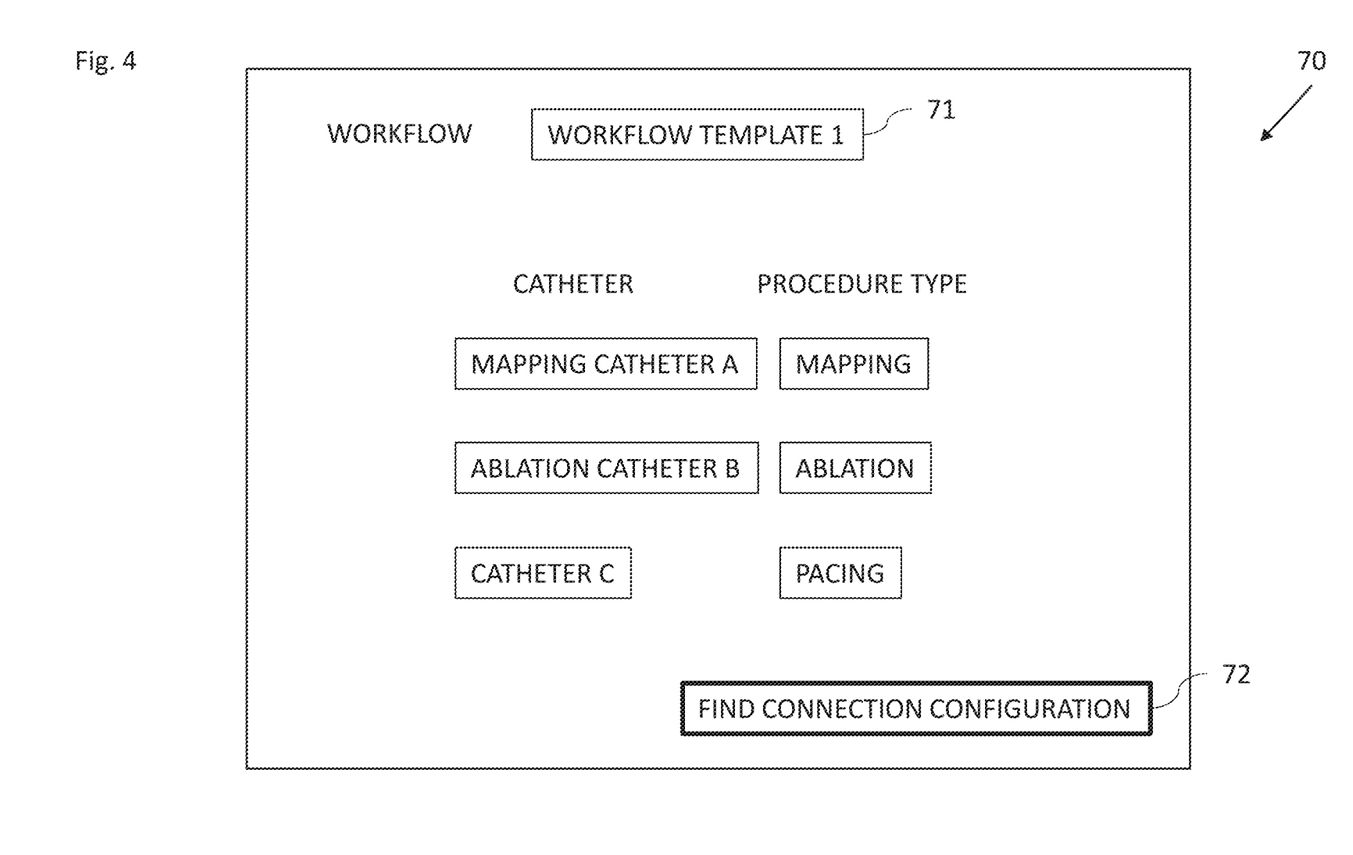
FIG. 4 is a schematic view of a user interface screen to select catheters for use in the system of FIG. 1.

Reference is now made to FIGS. 3 and 4. FIG. 3 is a flowchart 100 including steps in a method of operation of the system 20 of FIG. 1. FIG. 4 is a schematic view of a user interface screen 70 to select catheters 40 for use in the system 20 of FIG. 1. The processing circuitry 41 is configured to receive user input selecting respective ones of the catheters 40 to be used in a medical procedure (block 102).

In some examples, the processing circuitry is configured to receive user input selecting at least one procedure type (e.g., mapping or ablation) to be performed during the medical procedure. The catheters 40 and optionally the procedure types may be selected using the user interface screen 70 rendered to the display 27 as shown in FIG. 4.

In some examples, the processing circuitry 41 is configured to receive user input selecting a workflow template (input field 71) thereby selecting the catheters 40 to be used in a medical procedure. For example, one or more physicians may save different workflow templates including the catheters 40 used in the workflow and optionally associated procedure types performed by each catheter 40. The selected workflow template may be retrieved from the memory 51 thereby selecting the catheters 40 (and procedure types) to be used. The catheters 40 and optionally the procedure types to be performed in the selected workflow template are displayed on the display 27. The displayed catheters 40 and procedure types may be changed by the physician 30.

Once the catheters 40 and the procedure types have been selected, the physician 30 may select the "find connection configuration" button 72 for the processing circuitry 41 to proceed to find the connection configuration of the selected catheters 40 with the ports 46.

In some examples, the processing circuitry 41 is configured to set at least one of the respective electrical channel profiles of the selected catheter(s) 40 responsively to the corresponding procedure type(s) (block 104). For example, if one of the selected catheters 40 has mapping electrodes and ablation electrodes, and the procedure type selected for that catheter is mapping, the ablation channels of that catheter do not need to be coupled with the ablation circuitry in the console 24 and therefore, the ablation channels of that catheter may be ignored when finding the connection configuration.

In some examples, the processing circuitry 41 is configured to match the respective electrical channel profiles of the respective selected catheters 40 to the respective electrical channel profiles of respective ones of the ports 46 and the respective electrical channel profiles of respective ones of the cables 38 (block 106). In some examples, the processing circuitry 41 is configured to match respective electrogram channel sets (and/or ablation channel sets and/or position signal channel sets) of the respective selected catheters 40 to respective electrogram channel sets (and/or ablation channel sets and/or position signal channel sets) of the respective ports 46 and the respective electrogram channel sets (and/or ablation channel sets and/or position signal channel sets) of respective ones of the cables 38. The number of channels as well as the arrangement of those channels (e.g., pin arrangements) in the connectors of the catheters 40, the ports 46 and the cables 38 (and the connectors of the cables 38) may be matched by the processing circuitry 41. The electrical channel profiles of the selected catheters 40 may be individually compared with the electrical channel profiles of the ports 46 and the cables 38 until an optimal connection configuration is found. In some examples, the connection configuration may be found in a more systematic fashion, for example using the matching process described with reference to FIG. 5. In some examples, connection configurations of different combination of catheters 40 with the ports 46 via different cables 38 may be pre-computed and saved so that when a given catheter combination is selected, the pre-computed optimal connection configuration may be retrieved from the memory 51.

Figure 5:
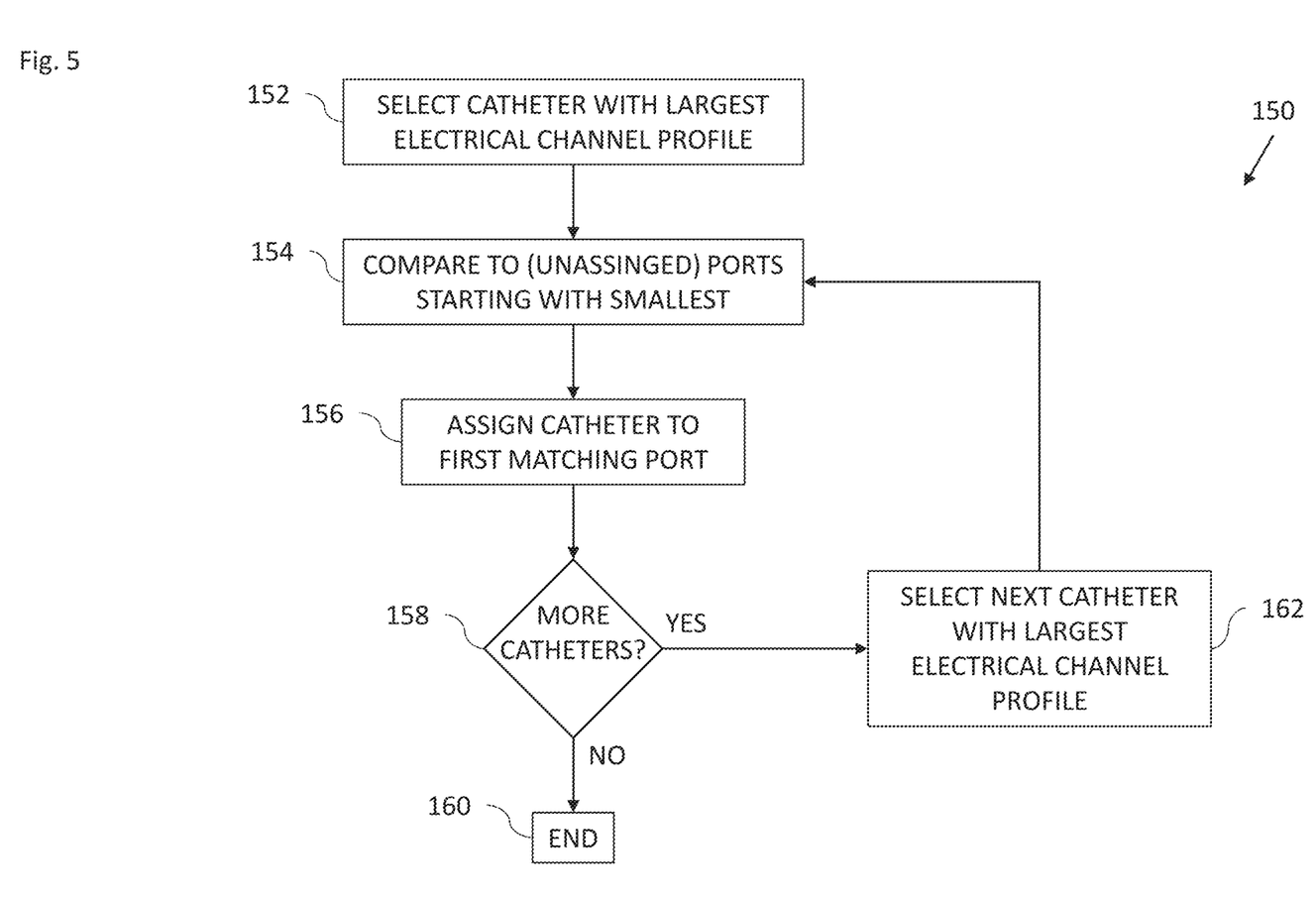
FIG. 5 is a flowchart including steps in a catheter matching sub-method of the method of FIG. 3.

Reference is now made to FIG. 5, which is a flowchart 150 including steps in a catheter matching sub-method of the method of FIG. 3. The processing circuitry 41 is configured to select from the selected catheters 40 (in the selection received in the step of block 102 (FIG. 3)), the catheter 40 with the largest electrical channel profile (e.g., the largest number of electrical connections or the largest number of electrogram channels etc.) (block 152). The processing circuitry 41 is configured to compare the electrical channel profile with the electrical channel profiles of the unassigned ports 46 optionally starting with the port 46 having the smallest electrical channel profile (block 154). Once a match is found in the step of block 154, the processing circuitry 41 is configured to assign the selected catheters 40 to the matching port 46 in the connection configuration (block 156). At a decision block 158, the processing circuitry 41 is configured to determine if there are more catheters 40 in the selection received in the step of block 102 (FIG. 3) to be matched using the above steps. If there are no more catheters 40 in the received selection to be matched using the above steps, the process ends (block 160). If there is one or more catheters 40 in the received selected to be matched using the above steps, the processing circuitry 41 is configured to select the next catheter 40 having the next largest electrical channel profile (block 162) and the steps of blocks 154-158 are repeated with the newly selected catheter. The above steps may also be used to find the correct cables 38 for the found catheter-port pairs.

Reference is again made to FIG. 4. If after performing the matching step of block 106, the processing circuitry 41 cannot find a connection configuration in which all the selected catheters 40 can be connected to the ports 46 at the same time, the processing circuitry 41 may then try to find a connection configuration in which the catheters 40 are connected during different time periods. For example, catheters 40 used for mapping may be connected for a first time period to the ports 46, and then the catheters 40 used for ablation may be connected for a second time period to the ports 46, based on the assumption that mapping is normally followed by ablation. Therefore, the processing circuitry 41 may be configured to prioritize an order of which ones of the selected catheters 40 to couple with the ports 46 of the console 24 responsively to the respective procedure type(s) that the selected catheters 40 will be used for (e.g., mapping or ablation) (block 108).

The processing circuitry 41 is configured to find the connection configuration with which to couple the respective selected catheters 40 with ones of the ports 46, responsively to (matching) the respective electrical channel profiles of the respective selected catheters 40 and the respective electrical channel profiles of the ports 46 (block 110). In some examples, the processing circuitry 41 is configured to find the connection configuration responsively to matching, for example, using the matching step of block 106 or the matching method described with reference to FIG. 5. In some examples, the processing circuitry 41 is configured to find the connection configuration with which to couple the respective selected catheters 40 with the ones of the ports 46 for the same time period during the medical procedure, responsively to (matching) the respective electrical channel profiles of the respective selected catheters 40 and the respective electrical channel profiles of the ports 46. In some examples, the processing circuitry 41 is configured to find the connection configuration with which to couple the respective selected catheters 40 with ones of the ports 46 via respective cables 38, responsively to the respective electrical channel profiles of the respective selected catheters 40, the respective electrical channel profiles of the ports 46, and respective electrical channel profiles of the respective cables 38.

The processing circuitry 41 is configured to find the connection configuration with which to couple the respective selected catheters 40 with ones of the ports 46 (and the cables 38), responsively to the respective electrical channel profiles of the respective selected catheters 40, the respective electrical channel profiles of the ports 46 (and the cables 38), and the procedure type(s) to be performed by the respective selective catheters 40 as described above with reference to the steps of blocks 104 and 108, which described how the procedure type(s) may affect finding the connection configuration.

Figure 6:
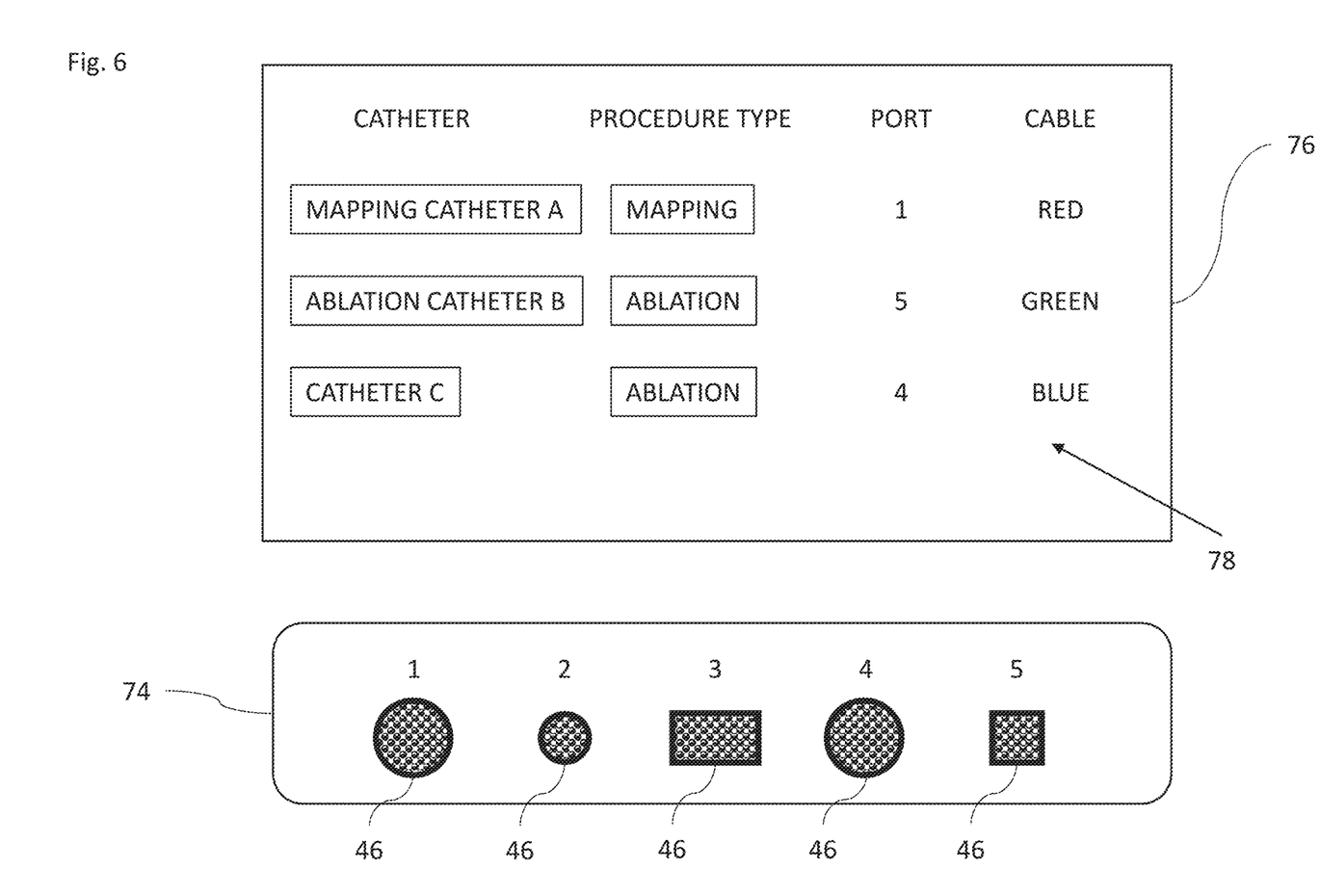
FIG. 6 is a schematic view of a port panel and a user interface screen showing a connection configuration in the system of FIG. 1.

Reference is now made to FIG. 6, which is a schematic view of a port panel 74 (in the console 24 of FIG. 1) and a user interface window 76 on display 27 showing a connection configuration 78 in the system 20 of FIG. 1. Reference is also made to FIG. 4. In some examples, the processing circuitry 41 is configured to render to the display 27 the connection configuration 78 comprising a mapping between the respective selected catheters 40 and respective indications of the ports 46 and the cables 38 (block 112).

In the example of FIG. 6, the ports 46 are provided with static (i.e., fixed) indications (e.g., labels), for example, using colors, shapes, names and/or numbers. The cables 38 and/or cable packaging 66 may also be labeled, for example, using colors, shapes, names and/or numbers. In the example of FIG. 6, the ports are labeled 1-5, the cables 38 are labeled using colors, and the connection configuration 78 rendered to the display 27 lists the port number and cable/cable packaging color for each of the selected catheters 40. For example, mapping catheter A (e.g., a basket catheter) should be connected to port 1 using the red cable, the ablation catheter B (e.g., a balloon catheter) should be connected to port 5 using the green cable, and catheter C (e.g., a focal catheter) should be connected to port 4 using the blue cable.

Figure 7:
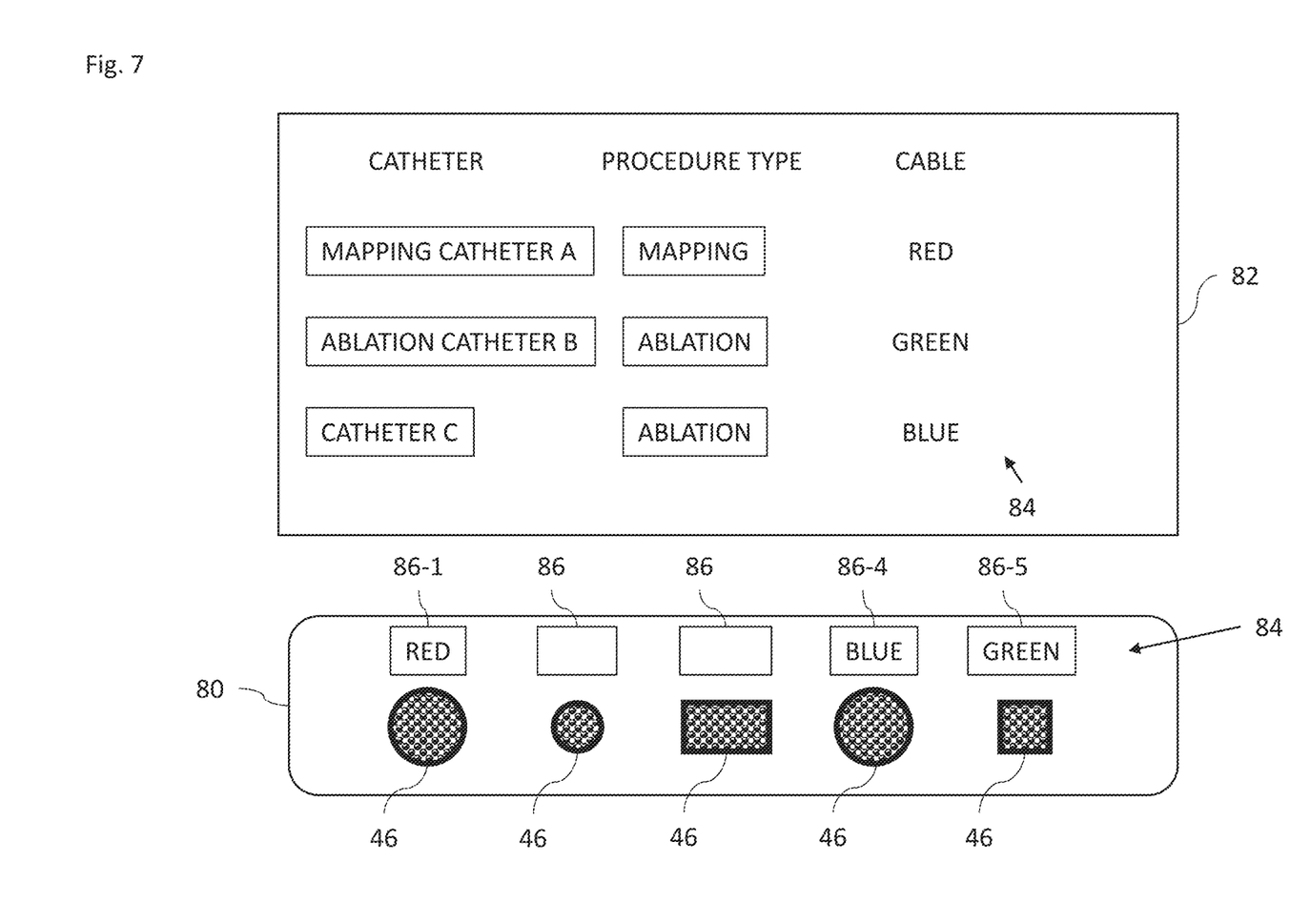
FIG. 7 is a schematic view of an alternative port panel and an alternative user interface screen showing a connection configuration in the system of FIG. 1.

Reference is now made to FIG. 7, which is a schematic view of an alternative port panel 80 and an alternative user interface screen 82 showing a connection configuration 84 in the system 20 of FIG. 1. In some examples, the system 20 may include respective port-displays 86 for the ports 46 with one port-display 86 per port 46. The processing circuitry 41 is configured to render to at least some of the port displays 86 respective indications of the respective cables 38 (e.g., by color, name, number or picture) that should be connected to respective ports 46 responsively to the connection configuration 84. The processing circuitry 41 is also configured to render to the display 27 indications of the respective cable 38 that should be connected to each catheter 40. For example, as shown in FIG. 7, the user interface screen 82 rendered on the display 27 indicates that mapping catheter A should be connected using the red cable, ablation catheter B should be connected using the green cable, and catheter C should be connected using the blue cable. The port displays 86-1, 86-5, 86-4, of ports 1, 5, and 4 display "red", "green", and "blue" using text, respectively, indicating how the cables 38 that should be connected to the ports 46. Alternatively, or additionally, the port-displays 86 may indicate the colors of the cables to be connected using a colored shape or colored text. In some examples, the port-displays 86 may be configured as ring-shaped liquid crystal displays (LCD) displays (controlled by software) that change color according to the cables to be attached to the respective ports 46.

Figure 8:
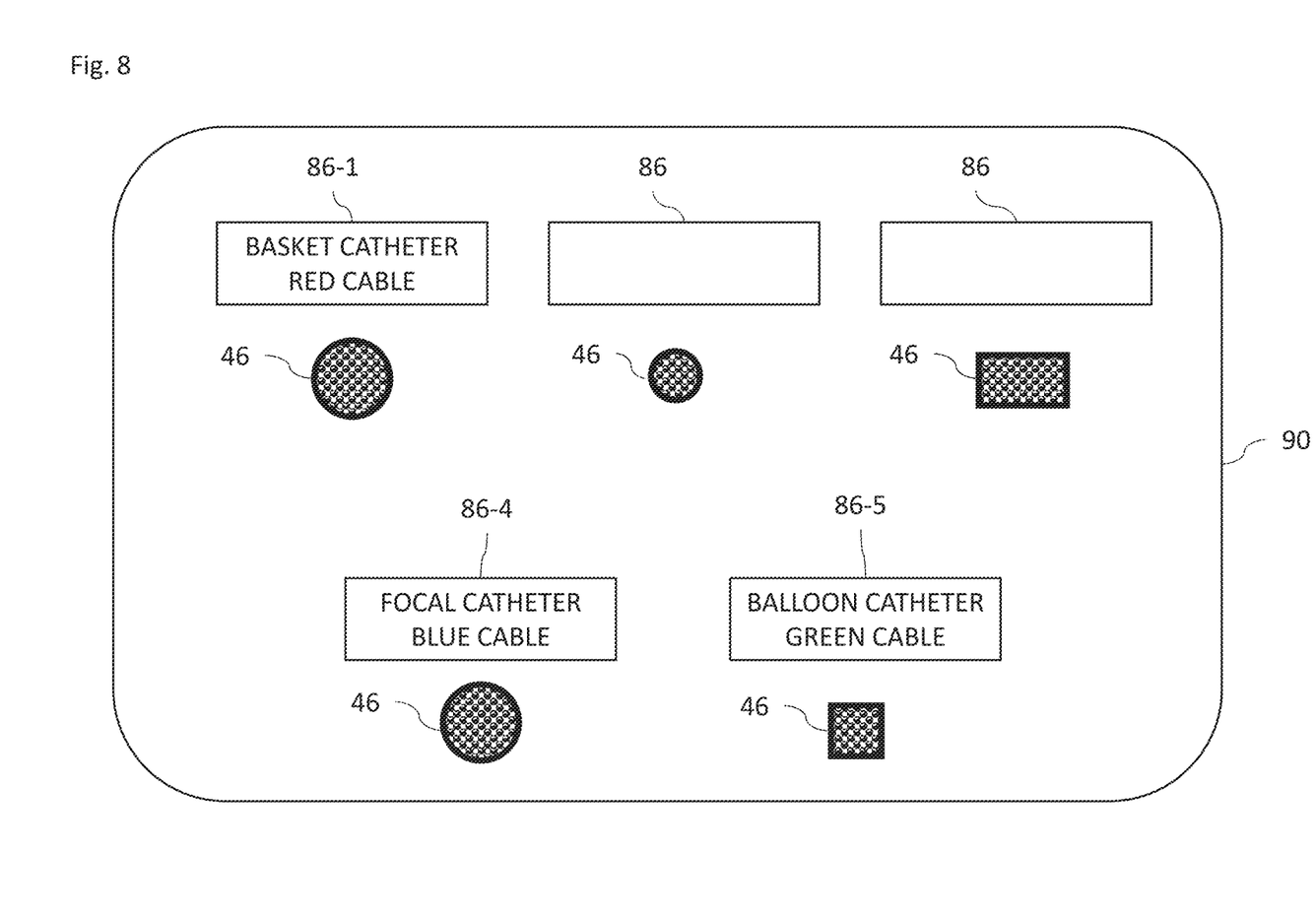
FIG. 8 is a schematic view of yet another alternative port panel for use in the system of FIG. 1.

Reference is now made to FIG. 8, which is a schematic view of yet another alternative port panel 90 for use in the system 20 of FIG. 1. In some examples, the processing circuitry 41 is configured to render to at least some of the port displays 86 indications of the respective selected catheters 40 and cables 38 that should be connected to respective ones of the ports 46 responsively to the connection configuration. For example, as shown in FIG. 8, the port display 86-1 of port 1 indicates that mapping catheter A should be connected using the red cable, the port display 86-5 of port 5 indicates that ablation catheter B should be connected using the green cable, and the port display 86 of port 4 indicates that catheter C should be connected using the blue cable.

Example 1

A medical system (20), including a display (27), a console (24) including a plurality of ports (46) configured to be coupled with the catheters (40) via respective cables (38), the catheters (40) having respective first electrical channel profiles, the ports (46) having respective second electrical channel profiles, and processing circuitry (41) configured to receive user input selecting respective ones of the catheters (40) to be used in a medical procedure, find a connection configuration with which to couple the respective ones of the catheters (40) with ones of the ports (46), responsively to the respective first electrical channel profiles of the respective ones of the catheters (40) and the respective second electrical channel profiles of the ports (46), and render the connection configuration to the display (27).

Example 2

The system (20) according to Example Chapter 11, wherein the processing circuitry (41) is configured to receive user input selecting a workflow template thereby selecting the respective ones of the catheters (40) to be used in a medical procedure.

Example 3

The system (20) according to Example Chapter 11 or Example 2, wherein the processing circuitry (41) is configured to find the connection configuration with which to couple the respective ones of the catheters (40) with the ones of the ports (46) for a same time period during the medical procedure, responsively to the respective first electrical channel profiles of the respective ones of the catheters (40) and the respective second electrical channel profiles of the ports (46).

Example 4

The system (20) according to any one of Examples Chapter 11 through 3, wherein the display (27) includes respective port-displays (86) for the ports (46), the processing circuitry (41) being configured to render to ones of the port displays indications of the respective ones of the catheters (40) that should be connected to respective ones of the ports (46) responsively to the connection configuration.

Example 5

The system (20) according to any one of Examples Chapter 11 through 4, wherein the processing circuitry (41) is configured to find the connection configuration with which to couple the respective ones of the catheters (40) with ones of the ports (46) via the respective cables (38), responsively to the respective first electrical channel profiles of the respective ones of the catheters (40), the respective second electrical channel profiles of the ports (46), and respective electrical channel profiles of the respective cables (38).

Example 6

The system (20) according to any one of Examples Chapter 11 through 5, wherein the cables (38) and the ports (46) are provided with indications, and the processing circuitry (41) is configured to render to the display (27) the connection configuration including a mapping between the respective ones of the catheters (40) and respective ones of the indications.

Example 7

The system (20) according to any one of Examples Chapter 11 through 6, wherein the indications are static.

Example 8

The system (20) according to any one of Examples Chapter 11 through 7, wherein the display includes respective port-displays (86) for the ports (46), the processing circuitry (41) being configured to render to ones of the port displays the respective ones of the indications of the respective ones of the cables (38) that should be connected to respective ones of the ports (46) responsively to the connection configuration.

Example 9

The system (20) according to any one of Examples Chapter 11 through 8, wherein the processing circuitry (41)

is configured to match the respective first electrical channel profiles of the respective ones of the catheters (40) to the respective second electrical channel profiles of respective ones of the ports (46), and find the connection configuration responsively to the matching.

Example 10

The system (20) according to any one of Examples Chapter 11 through 9, wherein the processing circuitry (41) is configured to match respective electrogram channel sets of the respective ones of the catheters (40) to respective electrogram channel sets of the respective ones of the ports (46).

Example 11

The system (20) according to any one of Examples Chapter 11 through 10, wherein the processing circuitry (41) is configured to receive user input selecting at least one procedure type to be performed during the medical procedure, and find the connection configuration with which to couple the respective ones of the catheters (40) with ones of the ports (46), responsively to the respective first electrical channel profiles of the respective ones of the catheters (40), the respective second electrical channel profiles of the ports (46), and the at least one procedure type.

Example 12

The system (20) according to any one of Examples Chapter 11 through 11, wherein the processing circuitry (41) is configured to prioritize an order of which ones of the respective ones of the catheters (40) to couple with the console (24) responsively to the at least one procedure type.

Example 13

The system (20) according to any one of Examples Chapter 11 through 12, wherein the processing circuitry (41) is configured to set at least one of the respective first electrical channel profiles responsively to the at least one procedure type.

Example 14

A medical system (20), including a plurality of catheters (40) having respective first electrical channel profiles, the catheters (40) being configured to be inserted into a body part of a living subject, a display (27), a console (24) including a plurality of ports (46) having respective second electrical channel profiles, and configured to be coupled with the catheters (40) via respective cables (38), and processing circuitry (41) configured to receive user input selecting respective ones of the catheters (40) to be used in a medical procedure, find a connection configuration with which to couple the respective ones of the catheters (40) with ones of the ports (46), responsively to the respective first electrical channel profiles of the respective ones of the catheters (40) and the respective second electrical channel profiles of the ports (46), and render the connection configuration to the display (27).

Example 15

A medical method, including receiving user input selecting respective catheters (40) to be used in a medical procedure, finding a connection configuration with which to couple the respective catheters (40) with ports (46) via respective cables (38), responsively to respective first electrical channel profiles of the respective catheters (40) and respective second electrical channel profiles of the ports (46), and rendering the connection configuration to a display (27).

Example 16

The method according to Example 15 includes receiving user input selecting a workflow template thereby selecting the respective ones of the catheters (40) to be used in a medical procedure.

Example 17

The method according to Example 15 or Example 16 includes finding the connection configuration with which to couple the respective catheters (40) with the ports (46) for a same time period during the medical procedure, responsively to the respective first electrical channel profiles of the respective catheters (40) and the respective second electrical channel profiles of the ports (46).

Example 18

The method according to Examples 15 through 17, wherein the rendering includes rendering to port displays indications of the respective catheters (40) that should be connected to respective ones of the ports (46) responsively to the connection configuration.

Example 19

The method according to Examples 15 through 18, wherein the finding includes finding the connection configuration with which to couple the respective catheters (40) with the ports (46) via the respective cables (38), responsively to the respective first electrical channel profiles of the respective catheters (40), the respective second electrical channel profiles of the ports (46), and respective electrical channel profiles of the respective cables (38).

Example 20

The method according to Examples 15 through 19, wherein the rendering includes rendering to the display (27) the connection configuration including a mapping between the respective catheters (40) and respective indications of the respective cables (38) and ports (46).

Example 21

The method according to Examples 15 through 20, wherein the indications are static.

Example 22

The method according to Examples 15 through 21, wherein the rendering includes rendering to port displays (86) the respective indications of the respective cables (38) that should be connected to respective ones of the ports (46) responsively to the connection configuration.

Example 23

The method according to Examples 15 through 22, wherein the method includes matching the respective first electrical channel profiles of the respective catheters (40) to the respective second electrical channel profiles of respective ones of the ports (46), and wherein the finding includes finding the connection configuration responsively to the matching.

Example 24

The method according to Examples 15 through 23, wherein the matching includes matching respective electrogram channel sets of the respective catheters (40) to respective electrogram channel sets of the respective ones of the ports (46).

Example 25

The method according to Examples 15 through 24, wherein the method includes receiving user input selecting at least one procedure type to be performed during the medical procedure, wherein the finding includes finding the connection configuration with which to couple the respective catheters (40) with ones of the ports (46), responsively to the respective first electrical channel profiles of the respective catheters (40), the respective second electrical channel profiles of the ports (46), and the at least one procedure type.

Example 26

The method according to Examples 15 through 25, wherein the method includes prioritizing an order of which ones of the respective catheters (40) to couple with the console (24) responsively to the at least one procedure type.

Example 27

The method according to Examples 15 through 26, wherein the method includes setting at least one of the respective first electrical channel profiles responsively to the at least one procedure type.

Example 28

A software product, including a non-transient computer-readable medium in which program instructions are stored, which instructions, when read by a central processing unit (CPU), cause the CPU to receive user input selecting respective catheters (40) to be used in a medical procedure, find a connection configuration with which to couple the respective catheters (40) with ports (46) via respective cables (38), responsively to respective first electrical channel profiles of the respective catheters (40) and respective second electrical channel profiles of the ports (46), and render the connection configuration to a display (27).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Various features of the disclosure which are, for clarity, described in the contexts of separate examples may also be provided in combination in a single example. Conversely, various features of the disclosure which are, for brevity, described in the context of a single example may also be provided separately or in any suitable sub-combination.

The examples described above are cited by way of example, and the present disclosure is not limited by what has been particularly shown and described hereinabove. Rather the scope of the disclosure includes both combinations and sub-combinations of the various features described hereinabove, as well as variations and modifications thereof which would occur to persons skilled in the art upon reading the foregoing description and which are not disclosed in the prior art.

What is claimed is:

1. A medical system, comprising:
   a display;
   a console comprising a plurality of ports configured to be coupled with catheters via respective cables, each of the catheters having respective first electrical channel profiles, each of the plurality of ports having respective second electrical channel profiles; and
   a processing circuitry configured to:
   receive user input selecting ones of the catheters to be used in a medical procedure;
   define a connection configuration with which to couple the ones of the catheters to ones of the plurality of ports, wherein the connection configuration defines at which of the plurality of ports each of the ones of the catheters are to be coupled;
   select ones of the respective cables as required by the connection configuration, responsively to the respective first electrical channel profiles of ones of the catheters and the respective second electrical channel profiles of ones of the plurality of ports; and
   render the connection configuration and the ones of the respective cables selected to the display.

2. The system according to claim 1, wherein the processing circuitry is configured to receive user input selecting a workflow template thereby selecting the ones of the catheters to be used in the medical procedure.

3. The system according to claim 1, wherein the processing circuitry is configured to find the connection configuration with which to couple the ones of the catheters with the ones of the plurality of ports for a same time period during the medical procedure, responsively to the respective first electrical channel profiles of the ones of the catheters and the respective second electrical channel profiles of ones of the plurality of ports.

4. The system according to claim 1, wherein the display includes respective port-displays for each of the plurality of ports, the processing circuitry being configured to render ones of the respective port-displays indications of the ones of the catheters that should be connected to respective ones of the plurality of ports responsively to the connection configuration.

5. The system according to claim 1, wherein the processing circuitry is configured to find the connection configuration with which to couple the respective ones of the catheters with the ones of the plurality of ports via the ones of the respective cables, responsively to the respective first electrical channel profiles of the ones of the catheters, the respective second electrical channel profiles of the ones of the plurality of ports, and respective electrical channel profiles of the ones of the respective cables.

6. The system according to claim 5, wherein:
   the ones of the respective cables and the ones of the plurality of ports are provided with indications; and
   the processing circuitry is configured to render to the display the connection configuration comprising a mapping between the ones of the catheters, the ones of the respective cables, and the indications.

7. The system according to claim 6, wherein the indications are static.

8. The system according to claim 6, wherein the display includes respective port-displays for the ones of the plurality of ports, the processing circuitry being configured to render to ones of the respective port displays the indications of the respective ones of the respective cables that should be connected to respective ones of the plurality of ports responsively to the connection configuration.

9. The system according to claim 1, wherein the processing circuitry is configured to:
match the respective first electrical channel profiles of the ones of the catheters to the respective second electrical channel profiles of respective ones of the plurality of ports; and
find the connection configuration and the ones of the respective cables responsively to the matching.

10. The system according to claim 9, wherein the processing circuitry is configured to match electrogram channel sets of the ones of the catheters to respective electrogram channel sets of the respective ones of the plurality of ports.

11. The system according to claim 1, wherein the processing circuitry is configured to:
receive user input selecting at least one procedure type to be performed during the medical procedure; and
find the connection configuration with which to couple the ones of the catheters with ones of the plurality of ports, responsively to the respective first electrical channel profiles of each of the catheters, the respective second electrical channel profiles of each of the ones of the plurality of ports, and the at least one procedure type.

12. The system according to claim 11, wherein the processing circuitry is configured to prioritize an order for coupling the catheters to the console responsively to the at least one procedure type.

13. The system according to claim 11, wherein the processing circuitry is configured to set at least one of the respective first electrical channel profiles responsively to the at least one procedure type.

14. A medical system, comprising:
a plurality of catheters having respective first electrical channel profiles, the plurality of catheters being configured to be inserted into a body part of a living subject;
a display;
a console comprising a plurality of ports having respective second electrical channel profiles, and configured to be coupled with the plurality of catheters;
a plurality of cables configured to couple the plurality of catheters to the plurality of ports; and
processing circuitry configured to:
receive user input selecting respective ones of the plurality of catheters to be used in a medical procedure;
find a connection configuration with which to couple the ones of the plurality of the catheters to the plurality of ports;
select ones of the plurality cables as required by the connection configuration, responsively to the respective first electrical channel profiles of the respective ones of the plurality of catheters and the respective second electrical channel profiles of the plurality of ports; and
render the connection configuration to the display.

15. A software product, comprising a non-transient computer-readable medium in which program instructions are stored, which instructions, when read by a central processing unit (CPU), cause the CPU to:
receive user input selecting respective ones of catheters to be used in a medical procedure;
find a connection configuration with which to couple the respective ones of the catheters with ports on a console;
select ones of the respective cables as required by the connection configuration, responsively to respective first electrical channel profiles of the respective ones of catheters and respective second electrical channel profiles of the ones of the plurality of ports; and
render the connection configuration and the respective cables selected to a display.

* * * * *